US012383402B2

(12) United States Patent
Clawson et al.

(10) Patent No.: US 12,383,402 B2
(45) Date of Patent: Aug. 12, 2025

(54) CRANIAL PLUG INCLUDING A LUCENT DISK

(71) Applicant: LONGEVITI NEURO SOLUTIONS, INC., Baltimore, MD (US)

(72) Inventors: Corbin Clawson, Hampstead, MD (US); Jimmy Shah, Hunt Valley, MD (US); Bradley Rabinovitz, Severna, MD (US)

(73) Assignee: LONGEVITI NEURO SOLUTIONS, INC., Baltimore, MD (US)

( * ) Notice: Subject to any disclaimer, the term of this patent is extended or adjusted under 35 U.S.C. 154(b) by 0 days.

(21) Appl. No.: 17/643,513

(22) Filed: Dec. 9, 2021

(65) Prior Publication Data

US 2022/0183844 A1    Jun. 16, 2022

Related U.S. Application Data

(60) Provisional application No. 63/123,557, filed on Dec. 10, 2020.

(51) Int. Cl.
| | |
|---|---|
| *A61B 90/10* | (2016.01) |
| *A61B 6/50* | (2024.01) |
| *A61B 8/08* | (2006.01) |
| *A61F 2/28* | (2006.01) |
| *A61F 2/30* | (2006.01) |

(52) U.S. Cl.
CPC ............ *A61F 2/2875* (2013.01); *A61B 6/501* (2013.01); *A61B 8/0808* (2013.01); *A61B 2090/103* (2016.02); *A61F 2002/30069* (2013.01); *A61F 2002/3009* (2013.01); *A61F 2310/00023* (2013.01)

(58) Field of Classification Search
CPC .......... A61F 2/2875; A61F 2002/30069; A61F 2002/3009; A61F 2310/00023; A61F 2/287; A61F 2/30723; A61F 2/4614; A61F 2002/2835; A61F 2002/30795; A61B 6/501; A61B 8/0808; A61B 2090/103; A61B 8/4209; A61B 8/4272; A61B 8/085; A61B 17/688; A61B 17/0057; A61B 17/12022; A61B 90/10
See application file for complete search history.

(56) References Cited

U.S. PATENT DOCUMENTS

| | | | | |
|---|---|---|---|---|
| 5,201,737 | A * | 4/1993 | Leibinger | A61B 17/8085 |
| | | | | 606/280 |
| 5,927,277 | A * | 7/1999 | Baudino | A61N 1/0539 |
| | | | | 600/386 |
| 6,044,304 | A * | 3/2000 | Baudino | A61N 1/0539 |
| | | | | 607/116 |
| 6,324,433 | B1 * | 11/2001 | Errico | A61N 1/0534 |
| | | | | 607/139 |
| 6,618,623 | B1 * | 9/2003 | Pless | A61N 1/37518 |
| | | | | 607/45 |

(Continued)

FOREIGN PATENT DOCUMENTS

| | | | | |
|---|---|---|---|---|
| AU | 2020232206 A1 * | 10/2021 | ........... | A61B 8/0808 |
| CN | 201899775 U * | 7/2011 | | |

(Continued)

*Primary Examiner* — Seema Mathew
(74) *Attorney, Agent, or Firm* — Welsh Flaxman & Gitler LLC (57) ABSTRACT

A cranial plug includes a cranial plug housing having a window recess with an access hole. A window is shaped and dimensioned for positioning with the window recess of the cranial plug housing.

13 Claims, 9 Drawing Sheets

(56) References Cited

U.S. PATENT DOCUMENTS

| | | | |
|---|---|---|---|
| 7,004,948 B1* | 2/2006 | Pianca | A61B 17/3462 607/116 |
| 10,631,946 B2* | 4/2020 | Loisel | A61B 90/10 |
| 11,497,914 B2* | 11/2022 | Hahn | A61N 1/36135 |
| 2004/0034367 A1* | 2/2004 | Malinowski | A61B 90/11 606/129 |
| 2007/0173844 A1* | 7/2007 | Ralph | A61B 17/688 606/916 |
| 2007/0233158 A1* | 10/2007 | Rodriguez | A61N 1/0539 606/130 |
| 2009/0112327 A1* | 4/2009 | Lane | A61B 90/10 623/16.11 |
| 2010/0023020 A1* | 1/2010 | Barker | A61B 90/50 606/129 |
| 2011/0270187 A1* | 11/2011 | Nelson | A61M 39/0208 604/151 |
| 2013/0304216 A1* | 11/2013 | Paspa | A61N 1/0539 623/17.19 |
| 2019/0192298 A1* | 6/2019 | Gordon | A61B 17/8061 |
| 2019/0282282 A1* | 9/2019 | Howard | A61B 17/688 |
| 2020/0030099 A1* | 1/2020 | Sampath | A61B 8/4416 |
| 2021/0121088 A1* | 4/2021 | Christopher | A61B 5/0022 |
| 2021/0260280 A1* | 8/2021 | Gordon | A61M 39/0247 |
| 2021/0330359 A1* | 10/2021 | Casey | B33Y 80/00 |
| 2022/0184383 A1* | 6/2022 | Clawson | A61B 90/10 |
| 2022/0296868 A1* | 9/2022 | Imran | A61M 39/0247 |
| 2023/0130616 A1* | 4/2023 | Clawson | A61N 1/0539 607/116 |
| 2024/0023923 A1* | 1/2024 | Clawson | A61B 8/488 |

FOREIGN PATENT DOCUMENTS

| | | | | |
|---|---|---|---|---|
| CN | 113171489 A | * | 7/2021 | |
| WO | WO-2018064239 A1 | * | 4/2018 | A61B 5/4064 |

* cited by examiner

CRANIAL PLUG INCLUDING A LUCENT DISK

CROSS REFERENCE TO RELATED APPLICATION

This application claims the benefit of U.S. Provisional Application Ser. No. 63/123,557, entitled "CRANIAL PLUG INCLUDING A LUCENT DISK," filed Dec. 10, 2020, which is incorporated herein by reference.

BACKGROUND OF THE INVENTION

1. Field of the Invention

The present invention relates to a cranial plug including a lucent disk.

2. Description of the Related Art

Transcranial access to the brain has become an increasingly important tool in neurosurgical procedures and neurological treatment. Whether one wishes to optically view the neuroanatomy directly through the skull, perform imaging of the neuroanatomy, or directly treat the neuroanatomy, access through the skull is important. The present invention provides mechanisms for accessing the neuroanatomy through the skull with the passage of light, sound, and/or radio waves in a manner that is safe, convenient, and effective.

SUMMARY

In one aspect a cranial plug includes a cranial plug housing having a window recess with an access hole and a window shaped and dimensioned for positioning with the window recess of the cranial plug housing.

In some embodiments wherein the cranial plug housing includes a first end, a second end, a first lateral side, a second lateral side, an upper surface, and a lower surface.

In some embodiments a recessed surface defining the window recess is formed along the upper surface of the cranial plug housing.

In some embodiments the cranial plug housing includes multiple chemically distinct materials.

In some embodiments the cranial plug housing includes a central body member made of a first material and a second material.

In some embodiments the first material is a sonolucent material.

In some embodiments the first material is polymethyl methacrylate or cubic zirconium.

In some embodiments the second material is flexible.

In some embodiments the second material is porous polyethylene or expanded polytetrafluoroethylene.

In some embodiments the access hole extending from the window recess to a lower surface of the cranial plug housing is shaped and dimensioned for passage of light, sound, and/or radio waves therethrough so as to access neuroanatomy for imaging and treatment.

In some embodiments the window is optically transparent.

In some embodiments the window is optically translucent to all light waves.

In some embodiments the window is sonolucent.

In some embodiments the window is radiolucent.

In some embodiments the window is optically transparent, optically translucent to all light waves, is sonolucent, and is radiolucent.

In some embodiments the window is a lucent disk.

In some embodiments the lucent disk includes an upper surface and a lower surface, and curvature of the upper surface differs from the curvature of the lower surface.

In some embodiments the lucent disk includes an alignment feature.

In some embodiments the alignment feature includes a series of markings at different depths within the lucent disk.

In some embodiments the lucent disk includes channels.

In another aspect a lucent burr hole plug includes a support frame having a central frame assembly defining a central opening. A lucent disk mounted upon the support frame, wherein the central opening is shaped and dimensioned for positioning of the lucent disk thereon in alignment with the central opening.

In some embodiments the support frame is a titanium support frame.

In some embodiments the central frame assembly includes an upper surface and a lower surface. The upper and lower surfaces are connected by an interior side wall and an exterior side wall, and a plurality of coupling arms radially extend outwardly from the exterior side wall.

In some embodiments each of the plurality of coupling arms includes a first end coupled to the central frame assembly and a second end positioned beyond a circumference define by the central frame assembly.

In some embodiments the lucent disk is optically transparent.

In some embodiments the lucent disk is optically translucent to all light waves.

In some embodiments the lucent disk is sonolucent.

In some embodiments the lucent disk is radiolucent.

In some embodiments the lucent disk is optically transparent, optically translucent to all light waves, is sonolucent, and is radiolucent.

Other objects and advantages of the present invention will become apparent from the following detailed description when viewed in conjunction with the accompanying drawings, which set forth certain embodiments of the invention.

DESCRIPTION OF THE EMBODIMENTS

The detailed embodiments of the present invention are disclosed herein. It should be understood, however, that the disclosed embodiments are merely exemplary of the invention, which may be embodied in various forms. Therefore, the details disclosed herein are not to be interpreted as limiting, but merely as a basis for teaching one skilled in the art how to make and/or use the invention.

Referring to FIGS. 1 to 6, various embodiments of a cranial plug 10 including a window in the form of a lucent disk 12 are disclosed. The cranial plug 10 is shaped and dimensioned for positioning within a physician formed cranial hole 100. The cranial plug 10 is further shaped and dimensioned for housing the lucent disk 12 in a reliable and secure manner. The cranial plug 10 includes a cranial plug housing 18. In accordance with the disclosed embodiment, the lucent disk 12 will be placed within the cranial plug housing 18, to create the cranial plug 10, at the time of surgery. It is, however, appreciated the lucent disk could be pre-formed within the cranial plug housing.

Figure 1:
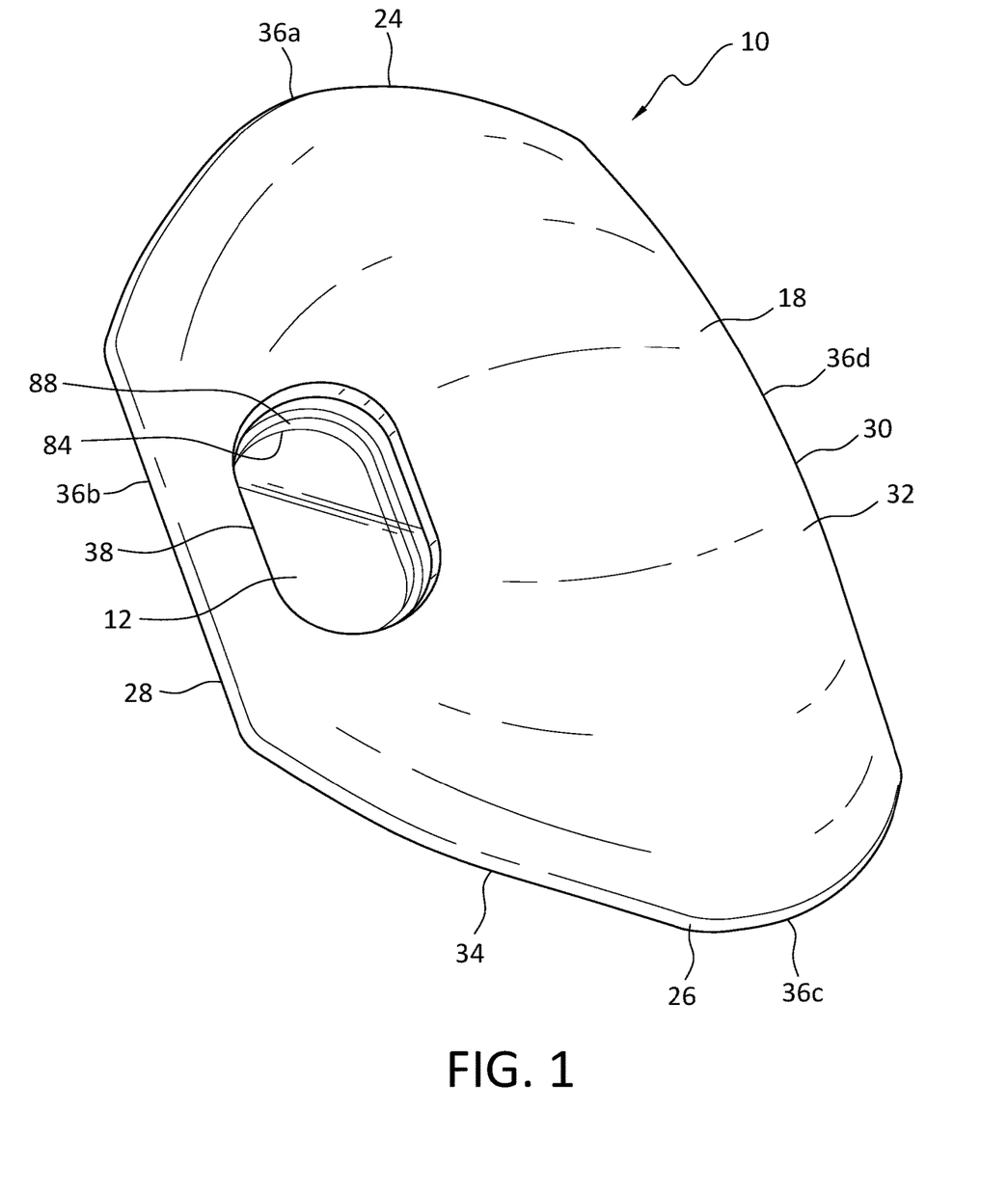
FIG. 1 is a top plan view of a cranial plug with a lucent disk.
Figure 2:
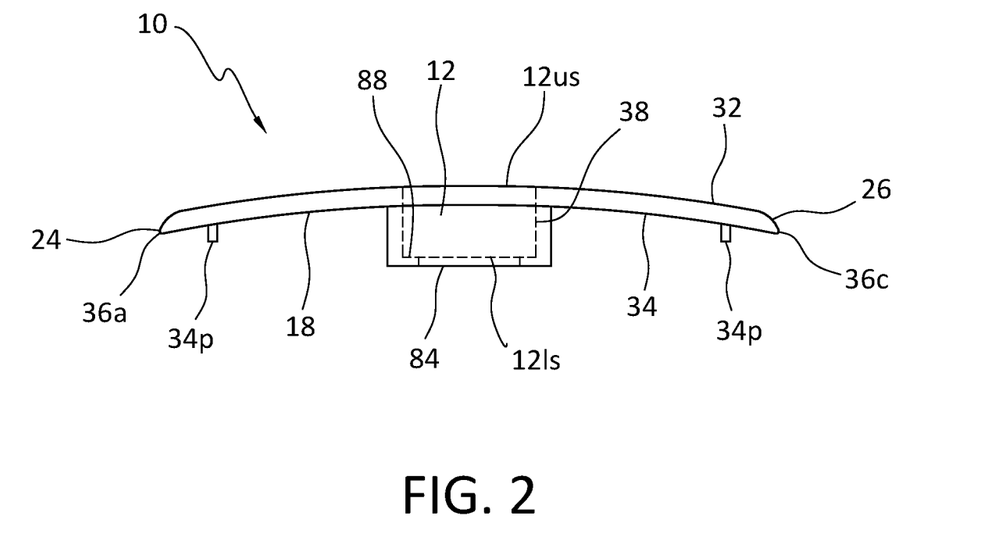
FIG. 2 is a cross sectional view of the lucent disk shown in FIG. 1.

The cranial plug housing 18 includes a first end 24, a second end 26, a first lateral side 28, and a second lateral side 30. The cranial plug housing 18 also includes an upper surface 32, a lower surface 34, and continuous side walls 36a-d extending between the upper surface 32 and the lower surface 34, as well as about the periphery of the cranial plug housing 18. As will be appreciated based upon the following disclosure, the lower surface 34 may be provided with a projection 34p that ultimately fits within the cranial hole 100 to assist in holding the cranial plug 10 in position after installation. In accordance with the disclosed embodiment, the projection 34p is defined by the outer wall of the window recess 38 in which the lucent disk 12 is positioned. With this in mind, the projection 34p is shaped to fit within the cranial hole 100.

While a particular shape of the cranial plug housing 18 in accordance with the disclosed embodiment is disclosed herein, it is appreciated various shapes may be employed within the spirit of the present invention. As such, the shape of the cranial plug and the mechanism for the creation of the cranial hole are intimately related and may be varied based upon needs and requirements. Further, in accordance with a disclosed embodiment the housing is made HDPE (high density porous polyethylene), although it is appreciated other materials, for example, polymethyl methacrylate (PMMA), polyether ether ketone (PEEK), silicon, or other biocompatible polymeric materials, may be used without departing from the spirit of the present invention.

A window recess 38 is formed within the upper surface 32 of the cranial plug housing 18. The window recess 38 is shaped and dimensioned for positioning of a lucent disk 12 therein. As such, and as will be appreciated based upon the following disclosure, the window recess 38 is provided with a central access hole 84 extending from the window recess 38 to the lower surface 34 of the cranial plug housing 18. The central access hole 84 is shaped and dimensioned for the passage of light, sound, and/or radio waves therethrough so as to access the brain for imaging and treatment.

The window recess 38 in which the lucent disk 12 is positioned, as well as the central access hole 84, is formed within the cranial plug housing 18. The window recess 38 is defined by recessed surface 88 formed along the upper surface 32 of the cranial plug housing 18. In particular, the recessed surface 88 defining the window recess 38 is formed along the upper surface 32 of the cranial plug housing 18. In accordance a disclosed embodiment, the central access hole is relatively large and is only slightly smaller than the diameter of the recess itself. As a result, the recessed surface positioned about the central access hole is made relatively small and is constructed to function as a ledge supporting the bottom surface of the lucent disk when it is positioned within the disk recess. By expanding the central access hole, unattenuated passage of light, sound, radio, and other waves will be optimized.

In accordance with an embodiment, the lucent disk 12 is optically transparent, optically translucent to all light waves, sonolucent (that is, allowing passage of ultrasonic waves without production of echoes that are due to the reflection of some of the waves), and/or radiolucent (that is, allowing passage of radio waves without production of echoes that are due to the reflection of some of the waves). Further still, and in accordance with a disclosed embodiment, the lucent disk is preferably made of polymethyl methacrylate (PMMA).

Through the provision of a lucent disk, a variety of options are available to medical practitioners wishing to provide the best treatment options to their patients. For example, the lucent disk may be manufactured in a manner allowing for the transmission of ultrasonic waves as described in U.S. Pat. No. 9,044,195, entitled "IMPLANTABLE SONIC WINDOW," ('195 Patent) which is incorporated herein by reference. As explained in the '195 Patent, a strong, porous sonically translucent material through which ultrasonic waves can pass for purposes of imaging the brain is employed, wherein the material is a polymeric material, such as polyethylene, polystyrene, acrylic, or poly(methyl methacrylate) (PMMA). In addition, U.S. Pat. No. 9,535,192, entitled "METHOD OF MAKING WAVEGUIDE-LIKE STRUCTURES," ('192 Publication) and U.S. Patent Application Publication No. 2017/0156596, entitled "CRANIAL IMPLANTS FOR LASER IMAGING AND THERAPY," ('596 Publication) both of which are incorporated herein by reference, making waveguide-like structures within optically transparent materials using femtosecond laser pulses wherein the optically transparent materials are expressly used in the manufacture of cranial implants. The '596 publication explains the use of optically transparent cranial implants and procedures using the implants for the delivery of laser light into shallow and/or deep brain tissue. The administration of the laser light can be used on demand, thus allowing real-time and highly precise visualization and treatment of various pathologies. Further still, Tobias et al. describe an ultrasound window to perform scanned, focused ultrasound hyperthermia treatments of brain tumors. Tobias et al., "ULTRASOUND WINDOW TO PERFORM SCANNED, FOCUSED ULTRASOUND HYPERTHERMIA TREATMENTS OF BRAIN TUMORS," Med. Phys. 14(2), March/April 1987, 228-234, which is incorporated herein by reference. Tobias et al. tested various materials to determine which material would best serve as an acoustical window in the skull and ultimately determined polyethylene transmitted a larger percentage of power than other plastics and would likely function well as an ultrasonic window. Further still, Fuller et al., "REAL TIME IMAGING WITH THE SONIC WINDOW: A POCKET-SIZED, C-SCAN, MEDICAL ULTRASOUND DEVICE," IEEE International Ultrasonics Symposium Proceedings, 2009, 196-199, which is incorporated herein by reference, provides further information regarding sonic windows.

Radiolucency allows a clinician to see the anatomy beneath the lucent disk 12 without "scatter" or interfering artifacts from the implant for diagnosis and follow-up. By another definition of radiolucency, radio waves are able to transmit easily through the lucent disk 12, for example, via Bluetooth or other frequency transmission; which can serve many purposes including, but not limited to, data management and controller telemetry. The provision of radiolucency also allows for the integration of markings (as discussed below) made with radiographic materials, for example, barium sulfate, to be visible in contrast to the remainder of the craniofacial implant to allow for unique device identifiers or unique patient information to be visible on postoperative scans.

Considering the provision of optical lucency in the lucent disk 12, the ability to optically transmit through the lucent disk 12 allows for visualization of anatomy distal to the lucent disk 12, allows for the potential of higher bandwidth optical links (similar to radio transmission) between proximal adjunct devices, allows for light to be emitted through the lucent disk 12 to adjacent anatomy which could aid in optogenetics, and allows for imaging/therapeutic modalities that rely on light like optical coherence tomography from within the implant.

It is appreciated that the housing of the cranial plug may be further modified to improve positioning and identification thereof through the inclusion of various structural elements as disclosed in Applicant's own U.S. Patent Application Publication No. 2018/0304055, entitled "CEREBRAL SPINAL FLUID SHUNT PLUG," published Oct. 25, 2019, which is incorporated herein by reference. Briefly, physical bumps, an RFID (radio-frequency identification) device, and/or radiographic and/or acoustic properties may be incorporated into the housing.

Figure 3:
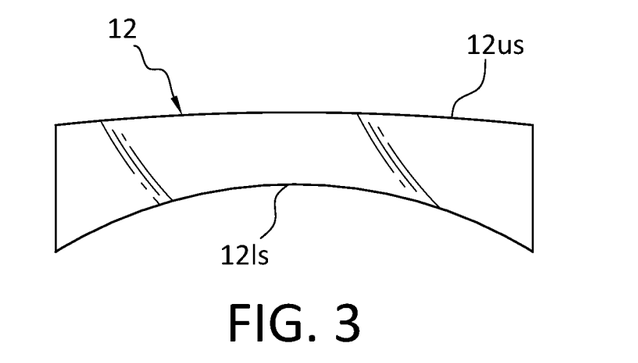
FIGS. 3, 4, and 5 are cross sectional views showing various embodiments of a lucent disk.

In accordance with one embodiment as shown with reference to FIG. 3, the lucent disk 12 may be constructed with variations in shape designed to control the manner in which light, sound, radio, and other waves pass therethrough that is, lensing or the focusing of light, sound, radio, and other waves by adjusting the thickness and/or curvature of the cranial implant. Such variations in shape would be undertaken in a manner similar to the way in which eyeglasses are adjusted for each patient. For example, and with reference to the disclosed embodiment, the curvature of the upper surface 12us differs from the curvature of the lower surface 12ls wherein the upper surface 12us has a much larger radius of curvature.

Figure 4:
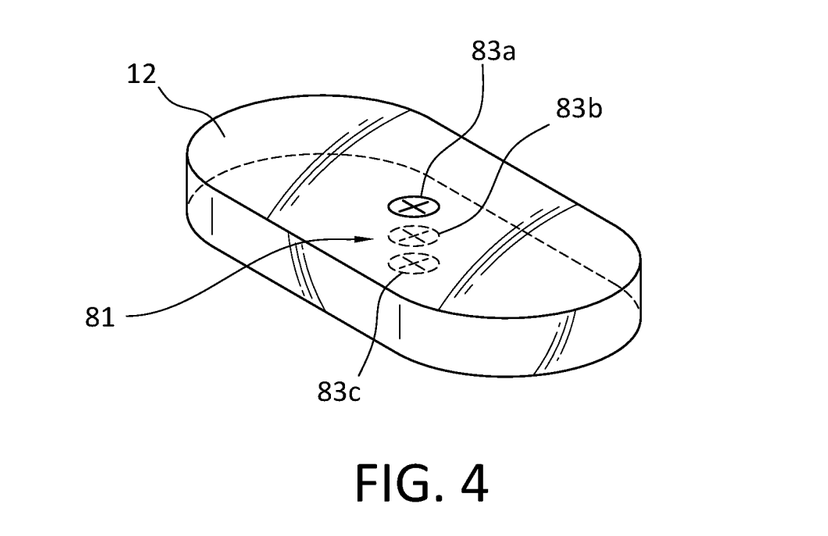

In accordance with another embodiment as shown with reference to FIG. 4, the lucent disk 12 may be constructed with an alignment feature 81. In accordance with a disclosed embodiment, the alignment feature 81 includes a series of markings 83a-c at different depths within the lucent disk. For example, an outer first lucent disk marking 83a and an inner second lucent disk marking 83b are formed along the upper and lower surfaces 80us, 80ls, respectively, of the lucent disk 80. A one or more additional interior lucent disk markings 80c may be formed within the body of the lucent disk 80 and in alignment with the outer first lucent disk marking 83a and an inner second lucent disk marking 83b. While an outer first lucent disk marking 83a, an inner second lucent disk marking 83b, and at least one additional interior lucent disk marking 83c are disclosed herein, it is appreciated various combinations of markings may be used within the spirit of the present invention.

The outer first lucent disk marking 83a, the inner second lucent disk marking 83b, and the plurality of additional interior lucent disk markings 83c are aligned such that when a transmitter of light, sound, radio, or other waves is properly aligned with the markings, the light, sound, radio, or other waves will be directed to the proper location within the cranium. Similar, when one looks through the lucent disk 12 and the outer first lucent disk marking 83a, the inner second lucent disk marking 83b, and the at least one additional interior lucent disk markings 83c merge into a single location identifying image (for example, crosshairs or circles), a specific brain anatomy (or other structural element upon the surface of the brain) is identified by the single location identifying image. When the specific brain anatomy identified by the single location identifying image changes over time, the surgeon will know that something has shifted and will take appropriate action.

Figure 5:
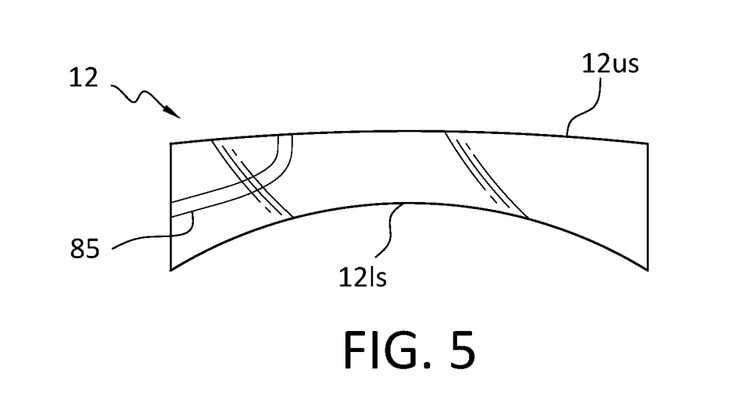

In accordance with one embodiment as shown with reference to FIG. 5, the lucent disk 12 may be constructed with wire channels 85 oriented for various purposes specific to different patients and treatment protocols.

With the inclusion of a lucent disk 12 with the cranial plug 10, positioning of the cranial plug 10 becomes important. As such, the installation procedure is as described below.

Installation of the cranial plug may be completed in a manner similar to that disclosed in U.S. Patent Application Publication No. 2018/0304055, entitled "CEREBRAL SPINAL FLUID SHUNT PLUG," published Oct. 25, 2019, which is incorporated herein by reference. The procedures described in the '055 publication, however, may be supplemented with positioning technology as described below. As those skilled in the art will appreciate, proper positioning of the lucent disk 12 is important.

In practice, and prior to initiating the surgical procedure, virtual images of the cranial plug 10, including the lucent disk 12, are generated. Virtual images of the patient, including the approximate location of the cranial plug 10 are also generated.

The procedure is initiated by making a cranial incision and a cranial hole in the skull. The cranial hole is created utilizing a template matching the shape of the cranial plug 10. Ultimately, it is appreciated the cranial hole may be made using any method acceptable to those skilled in the art. Given the matching shape of the cranial hole and the cranial plug 10, the cranial plug 10 will fit snugly within the cranial hole thereby minimizing potential movement after completion of the procedure.

With the cranial hole completed, the cranial plug housing 18 is positioned within the cranial hole with the upper surface 32 facing upwardly. The lucent disk 12 is then secured within the window recess 38. In particular, the cranial plug housing 18 is mounted within the cranial hole such that the upper surface 32 is substantially flush with the outer surface of the skull and the projection 34-p along the lower surface 34 is positioned within the cranial hole. As such, portions along the periphery of the cranial plug housing 18 overlie the skull, and screws may be passed therethrough to facilitate secure attachment of the cranial plug 10 to the skull. It is, however, appreciated the exact positioning of the cranial plug 10 will vary based upon specific anatomical characteristics of the patient.

As those skilled in the art will appreciate, proper positioning of the lucent disk 12 is important to ensure it is positioned in alignment with the neuroanatomy of interest. In accordance with an embodiment of the present invention and with reference to FIG. 6, movement of the actual cranial plug 10, including the cranial plug housing 18 and the lucent disk 12, relative to the patient is monitored in real-time. This is achieved by the integration of tracking devices 12t, 18t (for example, tracking devices used with well-known optical navigation surgical systems) into or onto the respective cranial plug housing 18 and the lucent disk 12. Additional tracking devices may be applied to the patient in a manner known to those skilled in the art. It should be appreciated that the tracking devices 12t, 18t may take a variety of forms so long as the computer based surgical guidance system 200 is capable of identifying the real-time movement of the various components of the cranial plug 10 being tracked. For example, the tracking devices may take the form of external tracking devices attached to the cranial plug, tracking devices integrated into the cranial plug, or existing structures of the cranial plug that are readily identifiable via the sensing structure of the computer based surgical guidance system 200. Sensing may be achieved via various known techniques, including, but not limited to, infrared, electromagnetic, optical, or other sensing techniques.

Figure 6:
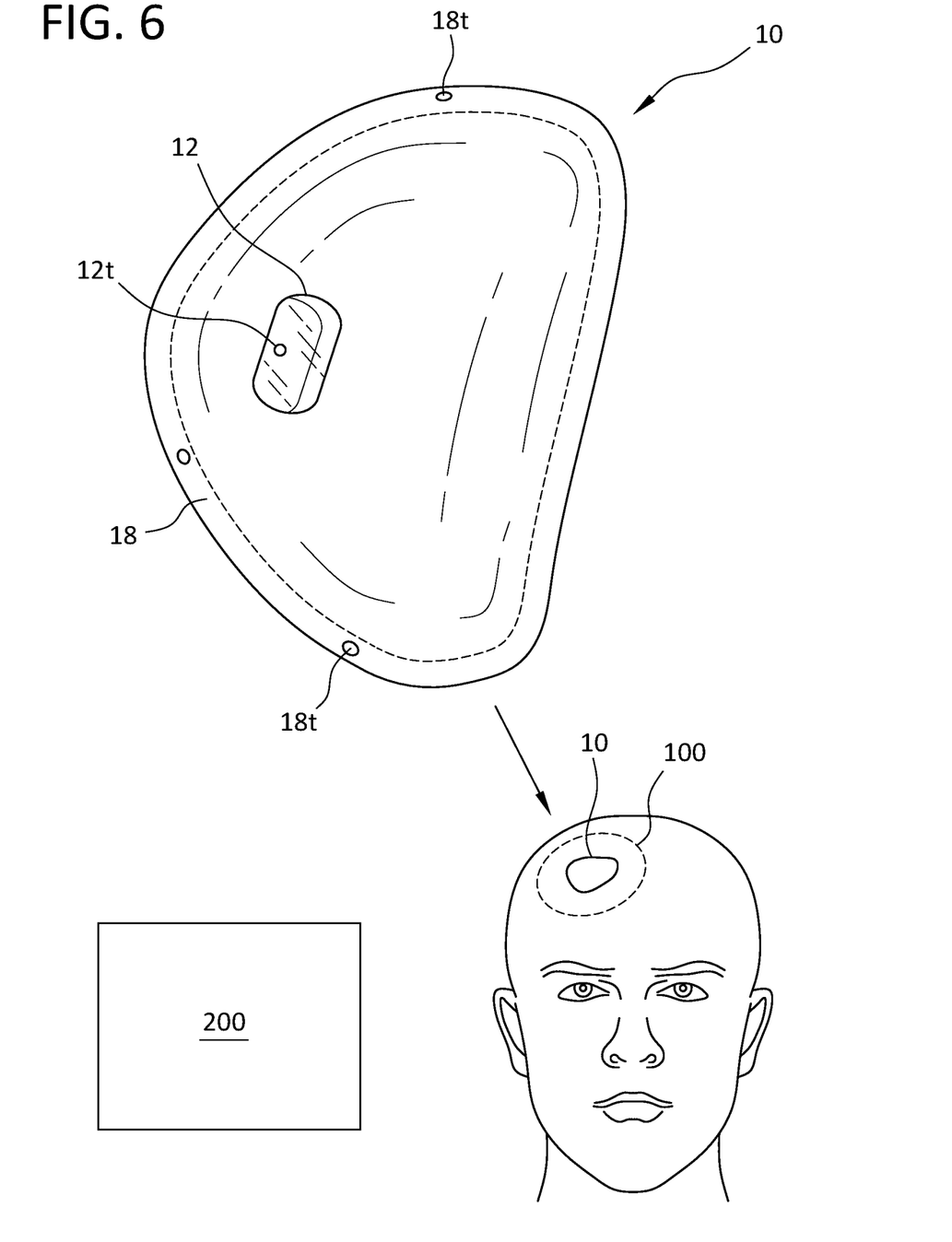
FIG. 6 is a schematic showing the process of implanting the cranial plug.

With the virtual images and the tracking devices, when used in conjunction with a computer based surgical guidance system 200, the cranial plug 10 is properly positioned within the patient.

Considering the fact the lucent disk is optically transparent, optically translucent to all light waves, sonolucent, and/or radiolucent, various features have been integrated into the lucent disk in an effort to enhance the functionality thereof. While these features are described herein as individual embodiments, it is appreciated they may be combined in various combinations as the needs of a patient dictate.

In accordance with one embodiment as shown with reference to FIG. 6, the lucent disk may be constructed with variations in shape designed to control the manner in which light, sound, radio, and other waves pass therethrough. Such variations in shape would be undertaken in a manner similar to the way in which eyeglasses are adjusted for each patient. For example, and with reference to the disclosed embodiment, the curvature of the upper surface differs from the curvature of the lower wherein the upper surface has a much larger radius of curvature.

While cranial plug housing of the various embodiments disclosed above are made of HDPE, it is appreciated the cranial plug housing may advantageously be made of clear PMMA. It is also contemplated, the cranial plug housing could be of a multi-material construction with the use of different materials in different elements of the cranial plug housing so as to expand the functionality thereof. The use of cranial plug housing made of clear PMMA in conjunction with the window offers a variety advantages. For example, the housing and the window could be made to offer different optical and sonolucent characteristics. For example, the housing and the window could be made to work with different ultrasound transducers or allow ultrasound transducers to focus upon different portions of the brain such that the system is optimized for imaging and interacting with the neuro anatomy, specifically the brain.

Because the attenuation of ultrasound signals passing through the housing and the window will be known, this information may be used to optimize imaging by selecting predefined operating characteristics for ultrasound transducers such that the ultrasound transducers are set to achieve specific imaging goals. The housing and window therefore defined specific locations for positioning of the ultrasound transducer so as to achieve specific diagnosis and treatment goals.

Figure 7:
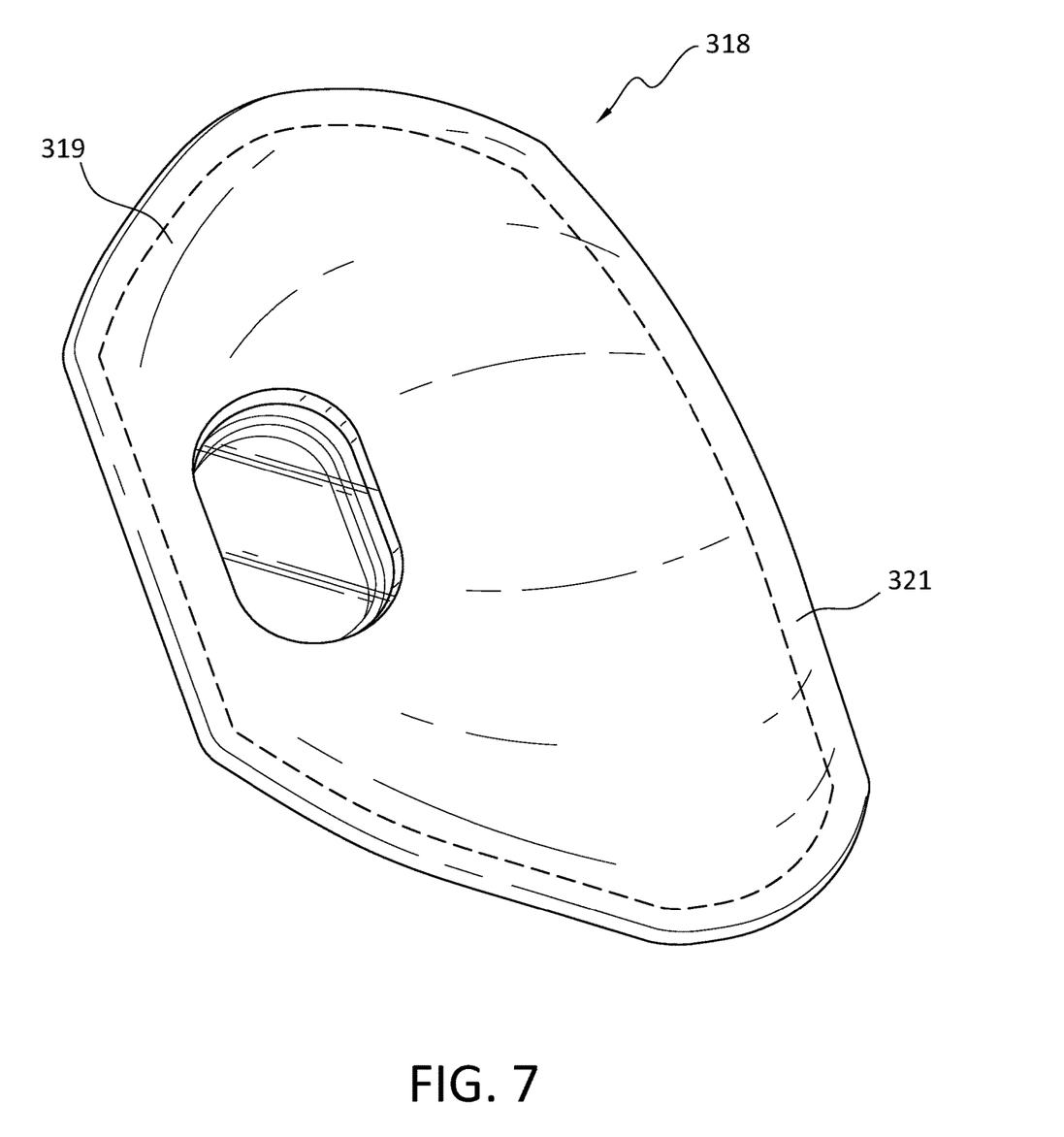
FIGS. 7, 8, and 9 are perspective views showing alternate embodiments of the cranial plug.

With regard to a dual material cranial plug, and with reference to FIG. 7, the cranial plug housing 318 includes a central body member 319 made of rigid sonolucent PMMA and a flexible perimeter member 321 made of porous polyethylene. Such a construction provides medical practitioners with a large sonolucent area for transcranioplasty ultrasound as provided by the central body member 319 and a malleable perimeter that optimizes a smooth transition between the implant perimeter and the native skull as provided by the flexible perimeter member 321. Such a flexible perimeter member could be made of expanded polytetrafluoroethylene (EPTFE), silicon, titanium, HDPE, polymethyl methacrylate (PMMA), polyether ether ketone (PEEK), or other biocompatible malleable material.

Figure 8:
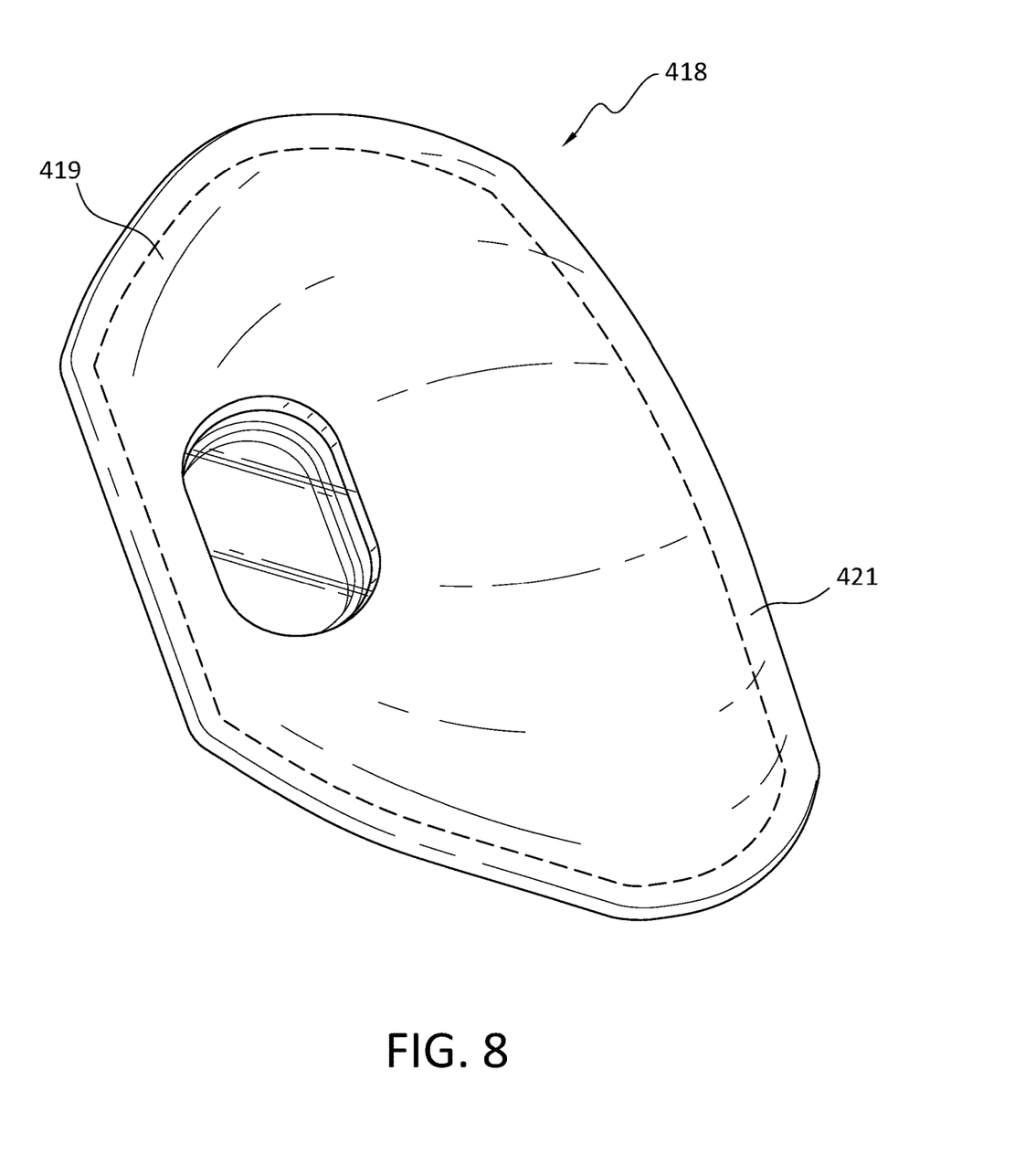

In accordance with another embodiment as shown with reference to FIGS. 8, the cranial plug housing 418 includes a central body member 419 made of cubic zirconium (or any other rigid sonolucent material) and a flexible perimeter member 421 made of expanded polytetrafluoroethylene (EPTFE), silicon, titanium, porous polyethylene, polymethyl methacrylate (PMMA), polyether ether ketone (PEEK), or other biocompatible malleable material.

Figure 9:
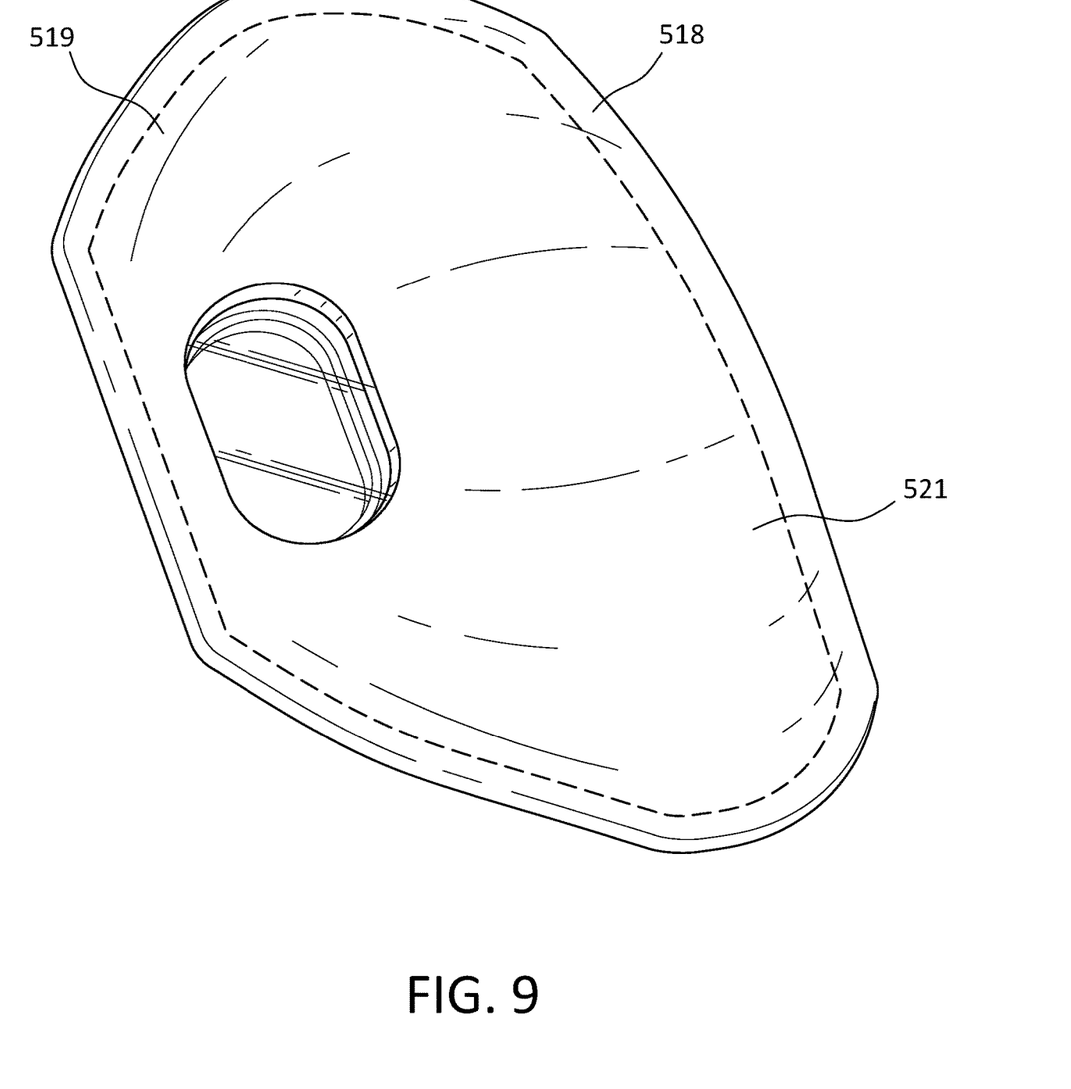

In accordance with yet another embodiment, as shown with reference to FIG. 9, the cranial plug housing 518 could be different compositions of the same material, with the different compositions being selected to enhance sonolucency and aesthetic fixation. For example, the central body member 519 of the cranial plug housing 518 could be rigid sonolucent PMMA while the flexible perimeter member 521 of the cranial plug housing could be PMMA with elastomer additives that changes its material properties from rigid to malleable. In this way the implant could have an optimal smooth transition from the perimeter of the implant to the native skull.

Figure 10:
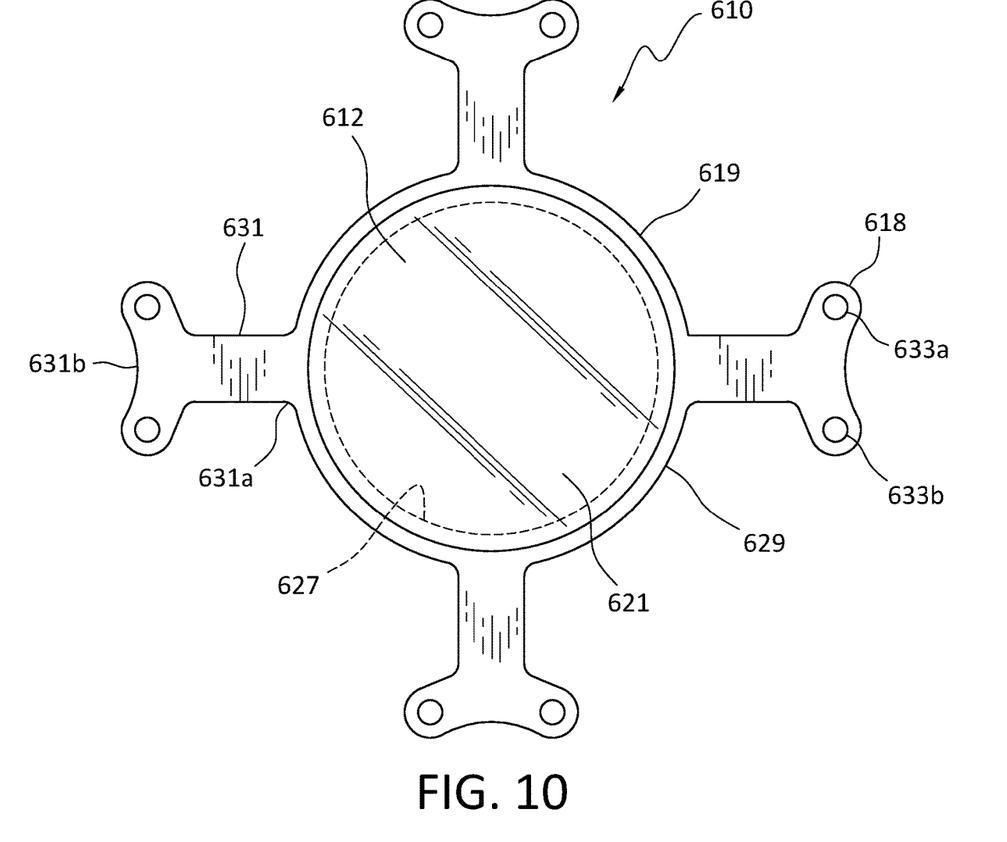
FIGS. 10 and 11 are respectively a top view and a cross sectional view of yet another embodiment.

In accordance with yet another embodiment, the concepts underlying the provision of a lucent window may be extended for use in conjunction with covering burr holes. With reference to FIG. 10, an embodiment is disclosed for a lucent burr hole plug 610. The lucent burr hole plug 610 includes a titanium support frame 618 upon which is mounted a lucent disk 612 similar to the lucent disks discussed above with reference to FIGS. 1 to 6. While titanium is used in accordance with a disclosed embodiment, other materials, for example, expanded polytetrafluoroethylene (EPTFE), silicon, titanium, porous polyethylene, polymethyl methacrylate (PMMA), polyether ether ketone (PEEK), or other biocompatible materials may be used.

In particular, the support frame 618 includes a circular central frame assembly 619 defining a central opening 621 shaped and dimensioned for the positioning of the lucent disk 612 thereon in alignment with the central opening 621. The central frame assembly 619 includes an upper surface 623 and a lower surface 625. The upper and lower surfaces 623, 625 are connected by an interior side wall 627 and an exterior side wall 629. While the central frame assembly 619 disclosed herein is of an annular configuration, it is appreciated other shapes may be used without departing from the spirit of the present invention.

The support frame 618 also includes a plurality of coupling arms 631 radially extending outwardly from the exterior side wall 629. In accordance with a disclosed embodiment, the support frame 618 includes four coupling arms 631. Each of the coupling arms 631 includes first end 631a coupled to the central frame assembly and a second end 631b positioned beyond the circumference defined by the central frame assembly 619. Each of the second ends 631b is provided with a first and second coupling apertures 633a, 633b for attaching the support frame 618 to the skull of a patient.

As briefly discussed above, the central opening 621 of the support frame 618 is shaped and dimensioned for positioning the lucent disk 612 thereon. Access through the lucent disk 612 and the central opening 621 is achieved without interference from the support frame 618.

As with the prior embodiments, the lucent disk 612 is optically transparent, optically translucent to all light waves, sonolucent (that is, allowing passage of ultrasonic waves without production of echoes that are due to the reflection of some of the waves), and/or radiolucent (that is, allowing passage of radio waves without production of echoes that are due to the reflection of some of the waves). Further still, and in accordance with a disclosed embodiment, the lucent disk is made of polymethyl methacrylate (PMMA).

Figure 11:
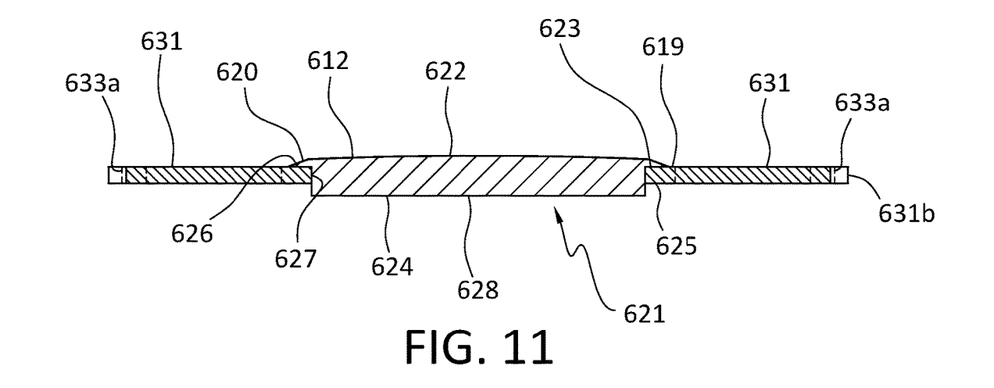

The lucent disk 612 of this embodiment includes an upper surface, a lower surface, and a sidewall 620 extending between the upper surface 622 and the lower surface 624. In order to facilitate the connection of the lucent disk 612 with the support frame 618, the lower surface 624 of the lucent disk 612 is formed with an outer perimeter 626 that conforms with the upper surface 623 of the circular central frame assembly 619 and a central portion 628 that conforms with the central opening 621 defined by the circular central frame assembly 619. The central portion 628 of the lucent disk 612 extends downwardly slightly more than the outer perimeter 626 such that the central portion 628 of the lucent disk 612 sits within the space defined by the central opening 621 of the circular central frame assembly 619 such that at least a portion of the lower surface 624 of the of lucent disk 612 connecting the outer perimeter 626 to the central portion 628 of the lucent disk 612 faces interior side wall 627 of the circular central frame assembly 619.

Secure attachment of the lucent disk 612 to the circular central frame assembly 619 is achieved by applying adhesive between the lucent disk 612 and the circular central frame assembly 619 wherein the outer perimeter 626 comes into contact with the upper surface 623 of the circular central frame assembly 619.

Figure 12:
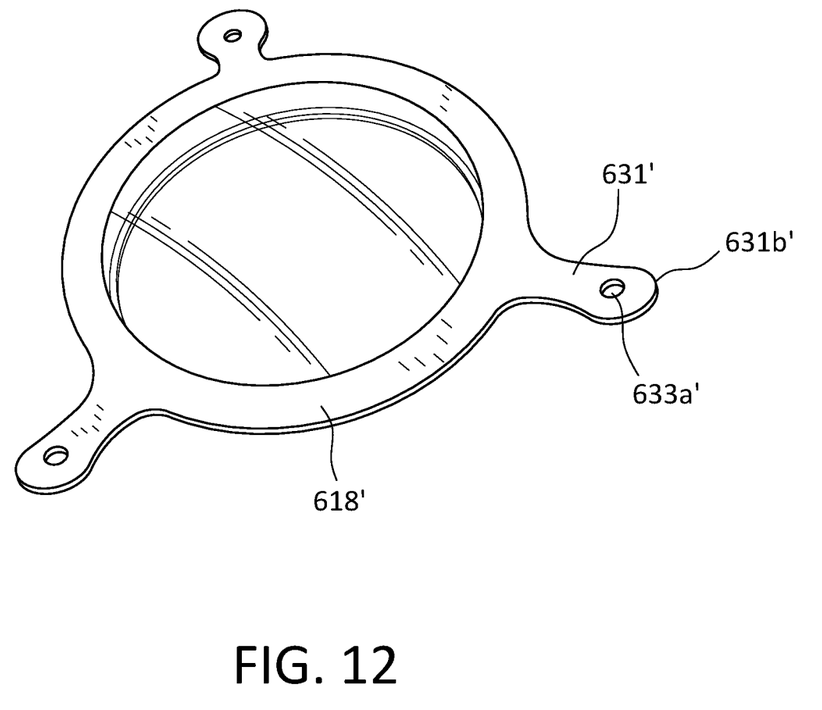
FIG. 12 is a top view of an alternate embodiment of the device shown in FIGS. 10 and 11.

As shown in FIG. 12, the embodiment shown in FIGS. 10 and 11 may be varied to accommodate different shapes. For example, the support frame 618' includes three coupling arms 631' and the each of the second ends 631b' is provided with a first coupling aperture 633a' for attaching the support frame 618' to the skull of a patient.

While the embodiment disclosed with reference to FIGS. 10 and 11 is disclosed as lucent burr hole plugs intended for direct mounting to the skull by positioning the lucent disk within a burr hole, it is appreciated the lucent burr hole plugs described herein could be employed as the lucent disk within the cranial plug housing of the embodiments described with reference to FIGS. 1 to 9.

While the embodiments have been shown and described, it will be understood that there is no intent to limit the invention by such disclosure, but rather, the disclosure is intended to cover all modifications and alternate constructions falling within the spirit and scope of the invention.

The invention claimed is:

1. A cranial plug, comprising:
a cranial plug housing including a first end, a second end, a first lateral side, a second lateral side, an upper surface, a lower surface, continuous side walls extending between the upper surface and the lower surface, a central body member, and a perimeter member;
the cranial plug housing including multiple chemically distinct materials, the central body member is made of a first material and the perimeter member is made of a second material, wherein the first material is a rigid sonolucent polymethyl methacrylate (PMMA) or rigid sonolucent cubic zirconium and the second material is flexible and is made of porous polyethylene, expanded polytetrafluoroethylene (EPTFE), silicon, high density porous polyethylene (HDPE), polymethyl methacrylate (PMMA), or polyether ether ketone (PEEK);
the upper surface of the cranial plug housing including a window recess with an access hole that extends from the window recess to the lower surface, the window recess is defined by a recessed surface formed along the upper surface; and
a window shaped and dimensioned for positioning within the window recess of the cranial plug housing.

2. The cranial plug according to claim 1, wherein the access hole extending from the window recess to a lower surface of the cranial plug housing is shaped and dimensioned for passage of light, sound, and/or radio waves therethrough so as to access neuroanatomy for imaging and treatment.

3. The cranial plug according to claim 1, wherein the window is optically transparent.

4. The cranial plug according to claim 1, wherein the window is optically translucent to all light waves.

5. The cranial plug according to claim 1, wherein the window is sonolucent.

6. The cranial plug according to claim 1, wherein the window is radiolucent.

7. The cranial plug according to claim 1, wherein the window is optically transparent, optically translucent to all light waves, is sonolucent, and is radiolucent.

8. The cranial plug according to claim 1, wherein the window comprises polymethyl methacrylate.

9. The cranial plug according to claim 1, wherein the window is a lucent disk.

10. The cranial plug according to claim 9, wherein the lucent disk includes an upper surface and a lower surface, and curvature of the upper surface differs from the curvature of the lower surface.

11. The cranial plug according to claim 9, wherein the lucent disk includes an alignment feature.

12. The cranial plug according to claim 11, wherein the alignment feature includes a series of markings at different depths within the lucent disk.

13. The cranial plug according to claim 9, wherein the lucent disk includes channels.

* * * * *